United States Patent
Kim et al.

(10) Patent No.: US 12,383,729 B2
(45) Date of Patent: Aug. 12, 2025

(54) ACUPOINT STIMULATION DEVICE AND ACUPOINT STIMULATION METHOD USING THE SAME

(71) Applicant: BRAINU CO., LTD., Seongnam-si (KR)

(72) Inventors: Kwang Moo Kim, Gyeonggi-do (KR); Seung Kyun Hong, Gwangmyeong-si (KR)

(73) Assignee: BRAINU CO., LTD., Seongnam-si (KR)

( * ) Notice: Subject to any disclaimer, the term of this patent is extended or adjusted under 35 U.S.C. 154(b) by 0 days.

(21) Appl. No.: 17/419,125

(22) PCT Filed: Nov. 16, 2020

(86) PCT No.: PCT/KR2020/016106
§ 371 (c)(1),
(2) Date: Jun. 28, 2021

(87) PCT Pub. No.: WO2021/145547
PCT Pub. Date: Jul. 22, 2021

(65) Prior Publication Data
US 2022/0331582 A1      Oct. 20, 2022

(30) Foreign Application Priority Data

Jan. 13, 2020 (KR) .................. 10-2020-0004234
Nov. 16, 2020 (KR) .................. 10-2020-0152733

(51) Int. Cl.
*A61N 1/36* (2006.01)
*A61N 1/04* (2006.01)
*A61N 1/40* (2006.01)

(52) U.S. Cl.
CPC ....... *A61N 1/0492* (2013.01); *A61N 1/36031* (2017.08); *A61N 1/403* (2013.01)

(58) Field of Classification Search
CPC .. A61N 1/0456; A61N 1/0484; A61N 1/0502; A61N 1/36007; A61N 1/36014;
(Continued)

(56) References Cited

U.S. PATENT DOCUMENTS 4,981,146 A     1/1991  Bertolucci
9,415,220 B1 *  8/2016  Spinelli ............. A61N 1/36036
(Continued)

FOREIGN PATENT DOCUMENTS

CN     107596555     1/2018
CN     108852821     11/2018
(Continued)

OTHER PUBLICATIONS

International Search Report for International Application No. PCT/KR2020/016106, dated Apr. 14, 2021.

*Primary Examiner* — Allen Porter
(74) *Attorney, Agent, or Firm* — KILE PARK REED & HOUTTEMAN PLLC

(57) ABSTRACT

The present disclosure relates to an acupoint stimulation device and an acupoint stimulation method using the same. The acupoint stimulation device includes: a power supply unit configured to supply power; a controller configured to generate an electrical stimulus signal applied to a skin of the subject; and an electrical stimulation unit including two or more electrodes configured to receive power from the power supply unit and to supply the stimulus signal to the acupoint area, wherein the electrodes are arranged in a state of being electrically insulated from each other and are in electrical contact with the skin of the subject. Thereby, it is possible to provide an appropriate amount of stimulation required for treatment and symptom relief by providing stimulation to an accurate acupoint position.

13 Claims, 15 Drawing Sheets

(58) Field of Classification Search
CPC ............ A61N 1/36017; A61N 1/36021; A61N 1/36034; A61N 1/36071
See application file for complete search history.

(56) References Cited

U.S. PATENT DOCUMENTS

| | | |
|---|---|---|
| 2003/0004555 A1 | 1/2003 | Giuntoli et al. |
| 2004/0044384 A1* | 3/2004 | Leber .................. A61N 5/0619 607/96 |
| 2014/0228927 A1 | 8/2014 | Ahmad et al. |
| 2015/0209584 A1 | 7/2015 | Escribano |
| 2016/0243359 A1* | 8/2016 | Sharma .................. A61N 5/025 |
| 2018/0116906 A1 | 5/2018 | Hirashiki et al. |
| 2019/0134396 A1 | 5/2019 | Toth et al. |
| 2019/0366076 A1* | 12/2019 | Simon ................ A61N 1/36025 |
| 2020/0138313 A1* | 5/2020 | Clements ............ A61B 5/6843 |
| 2020/0179691 A1* | 6/2020 | Chen .................... A61N 1/0452 |
| 2020/0353239 A1* | 11/2020 | Daniels ................ A61B 5/296 |
| 2021/0001124 A1* | 1/2021 | Brown .................... A61N 1/36 |

FOREIGN PATENT DOCUMENTS

| | | |
|---|---|---|
| FR | 3 051 110 | 11/2017 |
| JP | H09-182802 | 7/1997 |
| JP | 2019-531775 | 11/2019 |
| KR | 10-2009-0045876 | 5/2009 |
| KR | 10-1100718 | 12/2011 |
| KR | 10-2014-0030699 | 3/2014 |
| KR | 10-1405060 | 6/2014 |
| KR | 10-1669181 | 10/2016 |
| KR | 10-1715647 | 3/2017 |
| KR | 10-2018-0006132 | 1/2018 |
| KR | 10-2046051 | 11/2019 |
| WO | 2016/128985 | 8/2016 |
| WO | 2017/208167 | 12/2017 |
| WO | 2018039458 | 3/2018 |

* cited by examiner

ACUPOINT STIMULATION DEVICE AND ACUPOINT STIMULATION METHOD USING THE SAME

CROSS-REFERENCE TO RELATED APPLICATION(S)

This application is a national entry of International Application No. PCT/KR2020/016106, filed on Nov. 16, 2020, which claims priority to Korean Patent Application No. 10-2020-0004234 under 35 U.S.C. § 119, filed on Jan. 13, 2020 and Korean Patent Application No. 10-2020-0152733 under 35 U.S.C. § 119, filed on Nov. 16, 2020, the entire contents of which are hereby incorporated by reference.

BACKGROUND OF THE INVENTION

1. Field of the Invention

The present disclosure relates to an acupoint stimulation device and an acupoint stimulation method using the same. More particularly, the present disclosure relates to an acupoint stimulation device used for oriental medicine or manual therapy or the like so as to facilitate the flow of meridians to alleviate symptoms related to acupoints, which are important reaction points appearing on skin or muscles, and a method for stimulating acupoints using the acupoint stimulation device.

2. Description of the Prior Art

Traditional acupuncture therapy of oriental medicine is a method of treating diseases by piercing acupoints with an invasive metal needle to facilitate the flow of the meridians.

Recently, electro-acupuncture therapy and warm acupuncture therapy have been used in order to improve the effect of traditional acupuncture therapy.

Electro-acupuncture therapy is a therapy method that combines traditional acupuncture therapy with electrical stimulation using an electrical stimulator. Specifically, electro-acupuncture therapy is a therapy method, in which, after a metal needle is applied to the skin, a clip for transmitting electrical stimulation to the metal needle is attached to an acupuncture bottle so as to apply electrical stimulation to a corresponding acupoint.

Korean Patent No. 10-1405060 discloses an electric needle including a needle unit, in which a needle bottle forming the upper portion of a needle body has a spherical shape and is conductive, and an insulating layer, which is coated on the surface of the needle body.

However, this electro-acupuncture therapy is inconvenient because it is necessary to use the clip after coupling the clip to the metal needle. In addition, there is a disadvantage in that the orientation of the tip of the needle may be changed due to the bending of the metal needle applied to the skin due to the weight of the clip coupled to the upper portion of the metal needle. In particular, since a stimulus signal is transmitted to the metal needle in the form of a pulse wave, it is possible to set the magnitude of the signal. However, there is a problem in that it is difficult to provide an appropriate amount of stimulation required for treatment due to a short signal application time.

Warm acupuncture therapy is a combination of traditional acupuncture treatment and moxibustion. In order to enhance a therapeutic effect depending on the symptoms of disease, in the warm acupuncture therapy, a metal needle is applied to the skin and then a moxibustion column is fitted to the needle bottle (a needle handle). This warm acupuncture therapy is inconvenient, and may cause burns.

Korean Patent No. 10-2046051 discloses an electric warming acupuncture needle in which a space for storing therein a moxibution bar covering a needle body is formed inside a needle body, and the needle body includes a needle tip portion exposed to the outside of the needle bottle and transmitting an electrical stimulus signal supplied from the outside to the skin, and a needle frame portion disposed in the needle bottle and heated by current to ignite the moxibution bar.

This electric warming acupuncture needle has a problem in that the needle is bent due to the weight of the moxibustion rod. In addition, since the heat capacity of a human body is large, the electric warming acupuncture needle has a problem in that the amount of heat transferred from the moxibustion to the human body through the metal needle is low, and a therapeutic effect is low.

Meanwhile, a general electrical stimulator is a medical device that applies electrical stimulation to muscles or nerves of a human body for the purpose of pain relief, rehabilitation treatment, muscle exercise, or the like. Electrical stimulation may change the strength, waveform, and frequency of current.

Korean Patent No. 10-1669181 discloses a TENS apparatus including: an electric signal generator which generates an electrical stimulus signal; an electrode unit which transmits the electrical stimulus signal generated from the electric signal generator to a user via an electrode, and a connection means which connects the electric signal generator to the electrode unit, wherein the electrode unit includes a pair of ring-shaped contact points for electrical connection between the electric signal generator and the electrode unit.

When the conventional electrical stimulator described above is attached to the skin including an acupoint, the electrical stimulator stimulates a wide range of the skin. Therefore, there is a problem in that it is difficult to stimulate a deep local area in which an acupoint is located.

SUMMARY OF THE INVENTION

In order to solve the problems of the above-described background art, an aspect of the present disclosure is to provide an acupoint stimulation device that provides stimulation to an accurate acupoint by preventing the problem of stimulating an area other than an acupoint due to bending of a metal needle and an acupoint stimulation method using the acupoint stimulation device.

In addition, an aspect of the present disclosure is to provide an acupoint stimulation device that provides an appropriate amount of stimulation required for therapy and symptom relief, and an acupoint stimulation method using the acupoint stimulation device.

In addition, an aspect of the present disclosure is to provide an acupoint stimulation device that provides stimulation to a deep local area where an acupoint is located and an acupoint stimulation method using the acupoint stimulation device.

In order to solve the problems described above, the present disclosure provides an acupoint stimulation device for electrically stimulating an acupoint area of a subject including an acupoint and a portion around the acupoint. The acupoint stimulation device includes: a power supply unit configured to supply power; a controller configured to generate an electrical stimulus signal applied to a skin of the subject; and an electrical stimulation unit including two or more electrodes configured to receive power from the power supply unit and to supply the stimulus signal to the acupoint area. The electrodes are arranged in a state of being electrically insulated from each other and are in electrical contact with the skin of the subject.

Preferably, the electrical simulation unit includes a wiring layer on which wiring is formed to electrically connect the electrodes to each other, and an adhesive layer disposed under the wiring layer and including an adhesive detachably attached to the skin in the acupoint area. The electrodes are exposed to the bottom surface of the adhesive layer.

Preferably, the electrical simulation unit includes a body unit detachably attached to the subject and including two or more contact terminals configured to be in electrical contact with the acupoint area, and a mounting unit coupled to the body unit and including the electrodes. The electrodes are electrically connected to the contact terminals in the state in which the body unit and the mounting unit are coupled to each other.

Preferably, the mounting unit is fitted to the body unit.

Preferably, the mounting unit is aligned in position and coupled to the body unit by magnetic force.

Preferably, the electrical stimulation unit further includes a fixing unit configured to fix the contact terminals to be in close contact with the skin of the acupoint area.

Preferably, the fixing unit is formed in the form of a band made of an elastic material or in the form of a belt.

Preferably, in the electrical stimulation unit, the distance between the centers of two electrodes selected from among the electrodes is 5 mm to 30 mm in order to supply the stimulus signal to the acupoint area.

Preferably, the electrical stimulation unit includes three or more electrodes, and the controller is configured to apply the stimulus signal to electrode pairs each including two electrodes selected from among the electrodes.

Preferably, the controller is configured to alternately apply the stimulus signal to each of the electrode pairs.

Preferably, the acupoint stimulation device further includes a biosignal measurement unit configured to measure a biosignal of the subject, and the controller is configured to calculate a biometric level from the biosignal measured by the biosignal measurement unit, and to generate the stimulus signal by comparing the calculated biometric level with a preset target biometric level.

Preferably, the biosignal measurement unit includes a first biosignal measurement unit provided inside the acupoint stimulation device and configured to measure a biosignal from the skin at a location where the electrical stimulation unit is disposed, and the controller is a first controller provided inside the acupoint stimulation device.

Preferably, the biosignal measurement unit includes a first biosignal measurement unit provided inside the acupoint stimulation device, and the acupoint stimulation device further includes: a stimulation device communication unit provided inside the acupoint stimulation device and configured to transmit the biosignal measured by the first biosignal measurement unit and to receive the stimulus signal; and a user terminal including a terminal communication unit configured to receive the biosignal from the stimulation device communication unit and to transmit the stimulus signal, and a second controller configured to generate the stimulus signal according to the biosignal received from the terminal communication unit.

Preferably, the acupoint stimulation device further includes: a biometric information collector provided to be spaced apart from the electrical stimulation unit and including a second biosignal measurement unit constituting the biosignal measurement unit, and a collector communication unit configured to transmit a biosignal measured by the second biosignal measurement unit; and a user terminal including a terminal communication unit configured to receive the biosignal from the collector communication unit and transmit the stimulus signal to the stimulation device communication unit, and a second controller configured to generate the stimulus signal according to the biosignal received from the terminal communication unit; and a stimulation device communication unit provided inside the acupoint stimulation device and configured to receive the stimulus signal.

Preferably, the electrical stimulation unit includes three or more electrodes, and the controller is configured to: alternately apply the stimulus signal to each electrode pair including two electrodes selected from among the electrodes, calculate a biometric level from a biosignal according to each electrode pair to which the stimulus signal is applied, then set an electrode pair having a relatively superior biometric level among the biometric levels as a reference electrode pair, and apply the stimulus signal to the reference electrode pair.

Preferably, the electrical stimulation unit includes three or more electrodes, and the controller is configured to: measure a biopotential of each of the electrodes, calculate a biopotential similarity of each of the electrodes based on the biopotential, then set an electrode pair having a relatively high biopotential similarity as a reference electrode pair, and apply the stimulus signal to the reference electrode pair.

Preferably, the acupoint stimulation device further includes a temperature sensor unit configured to measure a skin temperature of the acupoint area, and the controller is configured to perform control such that supply of the stimulus signal is stopped when the temperature measured by the temperature sensor unit reaches a set temperature.

Preferably, the acupoint stimulation device further includes a temperature sensor unit configured to measure a skin temperature of the acupoint area, and a heating unit configured to receive power from the power supply unit so as to increase a temperature of a deep portion of the acupoint area. The controller is configured to perform control such that power supplied to the heating unit is cut off when the temperature measured by the temperature sensor unit reaches a set temperature.

Preferably, the heating unit is an induction coil that is disposed in parallel with a skin surface of the acupoint area in a state of being spaced apart from the electrodes so as to form an eddy current in the deep portion.

Preferably, the heating unit is an LED disposed between the electrodes so as to emit optical energy to the deep portion.

In order to solve the problems described above, another aspect of the present disclosure provides an acupoint stimulation method using the acupoint stimulation device described above. The acupoint stimulation method includes: disposing the acupoint stimulation device on an expected acupoint area of a subject; alternately applying a stimulus signal to electrode pairs each including two electrodes selected from among the electrodes; calculating a biometric level from a biosignal according to each electrode pair to which the stimulus signal is applied; setting an electrode pair having a relatively superior biometric level among the biometric levels as a reference electrode pair; and applying the stimulus signal to the reference electrode pair.

Preferably, an acupoint stimulation method using the acupoint stimulation device described above includes: disposing the acupoint stimulation device on an expected acupoint area of a subject; measuring a biopotential of each of the electrodes; calculating a biopotential similarity of each of the electrodes from the biopotential; setting an electrode having a relatively high biopotential similarity as a reference electrode pair; and applying a stimulus signal to the reference electrode pair.

According to an acupoint stimulation device and an acupoint stimulation method of the present disclosure, it is possible to provide an appropriate amount of stimulation required for treatment and symptom relief by providing stimulation to an accurate acupoint area.

In addition, according to the present disclosure, it is easy to detachably attach the acupoint stimulation device to the skin of an acupoint area by providing an adhesive layer.

In addition, according to the present disclosure, since the electrical stimulation unit includes the body unit and the mounting unit, it is possible to protect the electrodes provided in the mounting unit, and since the body unit and the mounting unit are coupled to each other through fitting or magnetic force, it is easy to detachably attach the acupoint stimulation device.

In addition, according to the present disclosure, since the acupoint stimulation device further includes a fixing unit, it is possible to fix the electrical stimulation unit to be in close contact with the skin.

In addition, according to the present disclosure, it is possible to provide stimulation not only to an acupoint but also to the periphery of the acupoint by alternately applying a stimulus signal to each of electrode pairs.

According to the present disclosure, since the acupoint stimulation device further includes the biosignal measuring unit, it is possible to compare a biometric level calculated from the measured biosignal with a target biometric level and to control a stimulus signal. From this, it is possible to provide a stimulus signal suitable for a current biometric state.

According to the present disclosure, since a stimulus signal is applied to an electrode pair having the highest biometric level among respective electrode pairs, it is possible to provide stimulation to an accurate acupoint area that improves the biometric level.

According to the present disclosure, since the position of an acupoint is determined from the biopotential similarity of each electrode and stimulation is provided to the accurate acupoint position, it is possible to effectively stimulate the acupoint in a local area.

According to the present disclosure, since the acupoint stimulation device further includes a temperature sensor unit, it is possible to prevent skin burns and damage by controlling the supply of a stimulus signal according to the skin temperature of the acupoint area.

In addition, according to the present disclosure, since the acupoint stimulation device further includes a heating unit, it is possible to increase the temperature of the deep portion of an acupoint area, thereby improving a stimulation effect and a biometric level, and it is possible to cut off power supplied to the heating unit according to the measured temperature, thereby preventing skin burns and damage.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION OF THE EXEMPLARY EMBODIMENTS

Hereinafter, embodiments of the present disclosure will be described in detail with reference to the accompanying drawings. An acupoint stimulation device of the present disclosure may be classified into first to third embodiments. The components of each embodiment are basically the same, but there are differences in some components.

The acupoint stimulation device of the present disclosure provides stimulation to an acupoint and an acupoint area including a portion around the acupoint. An acupoint is used for oriental medicine or manual therapy, and is an important reaction point that appears on skin or a muscle. In general, acupoint stimulation refers to stimulation of the acupoint below a subject's knee joint or nerves around the acupoint. By stimulating the acupuncture area, the flow of meridians is facilitated to relieve symptoms related to the acupoint or to aid in disease therapy. That is, the acupoint stimulation device of the present disclosure is a device that electrically stimulates a subject's acupoint area. Here, the subject means an animal including a human.

Figure 1:
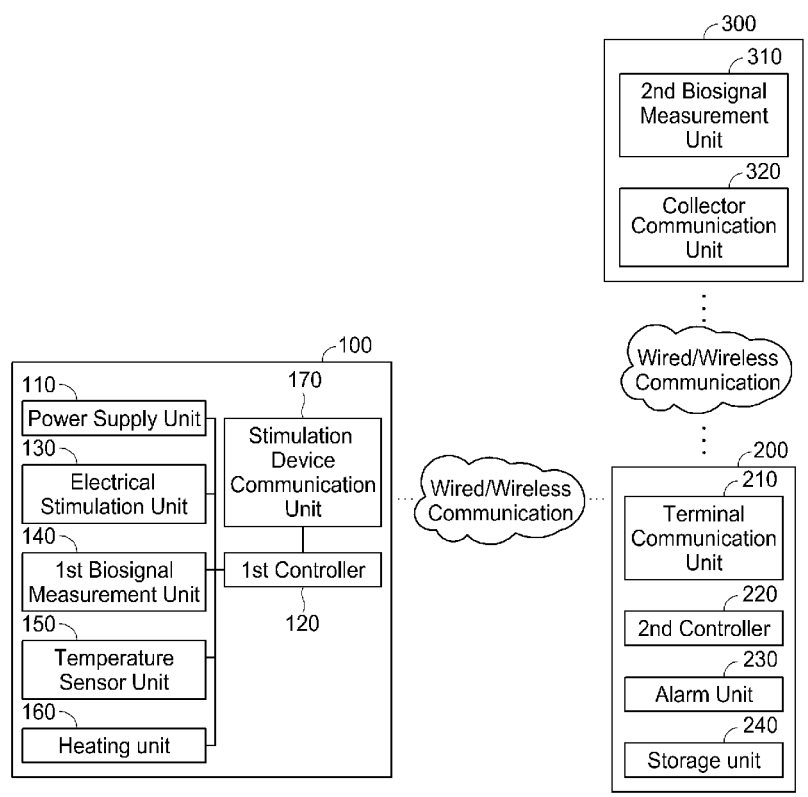
FIG. 1 is a block diagram illustrating an acupoint stimulation device of the present disclosure.

As illustrated in FIG. 1, the acupoint stimulation device according to the first embodiment includes a power supply unit 110, a controller, an electrical stimulation unit 130, a first biosignal measurement unit 140, a temperature sensor unit 150, and a heating unit 160.

The power supply unit 110 is connected to an external power supply or includes an internal power supply. The internal power supply of the power supply unit 110 may include a battery. The battery is rechargeable and can be used multiple times. In addition, the power supply unit 110 may be configured to be detachably attached to the electrical stimulation unit 130. The power supply unit 110 supplies power to the electrical stimulation unit 130, the first biosignal measurement unit 140, the temperature sensor unit 150, and the heating unit 160 when necessary.

The controller includes a first controller 120 provided inside the acupoint stimulation device.

The first controller 120 generates an electrical stimulus signal to be applied to a subject's skin. The first controller 120 applies the generated stimulus signal to the electrical stimulation unit 130.

The first controller 120 is provided in the acupoint stimulation device 100. The first controller 120 collects signals measured inside the acupoint stimulation device 100, processes the collected signals to generate a stimulus signal, and then applies the stimulus signal to the electrical stimulation unit 130 so as to control the electrical stimulation unit 130.

The electrical stimulation unit 130 supplies the stimulus signal generated by the first controller 120 to an acupoint area. The electrical stimulation unit 130 includes two or more electrodes. The electrodes are disposed in the state of being electrically insulated from each other, and are in electrical contact with the subject's skin.

The electrical stimulation unit 130 constituting the present disclosure may be classified into three types depending on the structure thereof.

Figure 2:
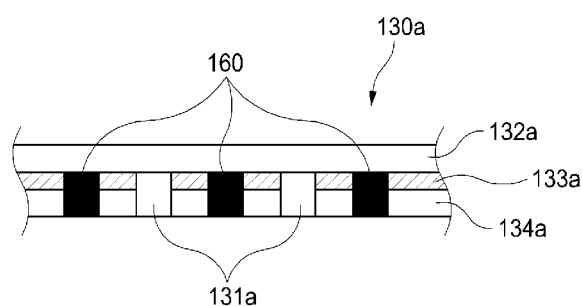
FIG. 2 is a cross-sectional view illustrating a first structure of an electrical stimulation unit constituting the present disclosure.

First, the electrical stimulation part 130a of a first type includes an electrode 131a, a base layer 132a, a wiring layer 133a, and an adhesive layer 134a, as illustrated in FIG. 2.

A plurality of electrodes 131a are provided, and a stimulus signal generated by a first controller 120 is supplied to an acupoint area.

The base layer 132a is a layer that determines the shape of the electrical stimulation unit 130a, and a plurality of electrodes 131a are disposed under the base layer 132a in an insulated state.

The wiring layer 133a is a layer on which a wiring electrically connecting the electrodes 131a disposed under the base layer 132a is formed. The wiring layer 133a is formed such that the wiring is connected to each of the electrodes 131a.

The adhesive layer 134a is disposed under the wiring layer 133a, and is made of an adhesive that is detachably attached to the skin of an acupoint area. In this case, the electrodes 131a are exposed to the bottom surface of the adhesive layer 134a. Accordingly, the electrodes 131a are in close contact with the skin such that the electrodes 131a are capable of more effectively supplying a stimulus signal to an acupoint area. The adhesive layer 134a is detachably attached to the skin by the adhesive, and thus allows the electrical stimulation unit 130a to be easily fixed to any portion of the body.

Figure 3:
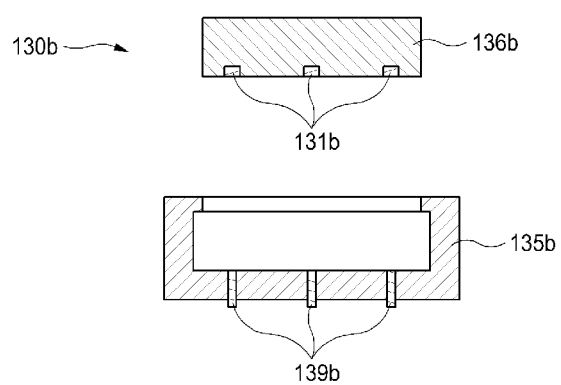
FIG. 3 is a cross-sectional view illustrating a second structure of the electrical stimulation unit constituting the present disclosure.
Figure 4:
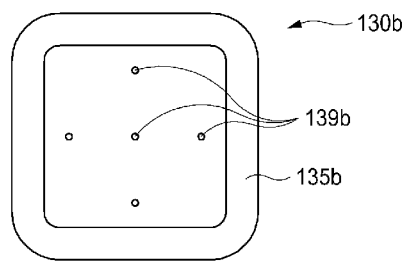
FIG. 4 is a plan view illustrating a body unit constituting the present disclosure.

The electrical stimulation unit 130b of the second type including a body unit 135b and a mounting unit 136b, as illustrated in FIGS. 3 and 4.

The body unit 135b is detachably attached to the skin of the object. The body unit 135b includes two or more contact terminals 139b to be in electrical contact with an acupoint area. The contact terminals 139b are in close contact with the skin.

The mounting unit 136b is fitted to the body unit 135b, and includes electrodes 131b provided to be exposed on the lower portion thereof. In this case, the body unit 135b is preferably formed to surround the side surface and a portion of the upper edge of the mounting unit 136b. Accordingly, the mounting unit 130b may be fitted into the body unit 135b. Although not illustrated in the drawings, the body unit may be formed to be fitted into the mounting unit.

The electrodes 131b and the contact terminals 139b are arranged to be electrically connected to each other in the state in which the body unit 135b and the mounting unit 136b are coupled to each other.

Accordingly, the user may easily attach and detach the mounting unit 136b in the state in which the body unit 135b is in close contact with the skin of a subject. In addition, the exposed portions of the electrodes 131b are protected by the body unit 135b so as to prevent contamination of the electrodes 131b, and are electrically connected to the skin via respective contact terminals.

Figure 5:
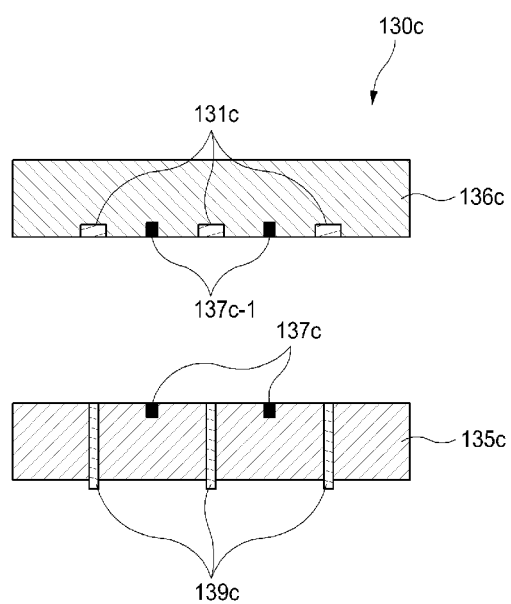
FIG. 5 is a cross-sectional view illustrating a third structure of an electrical stimulation unit constituting the present disclosure during assembly.
Figure 6:
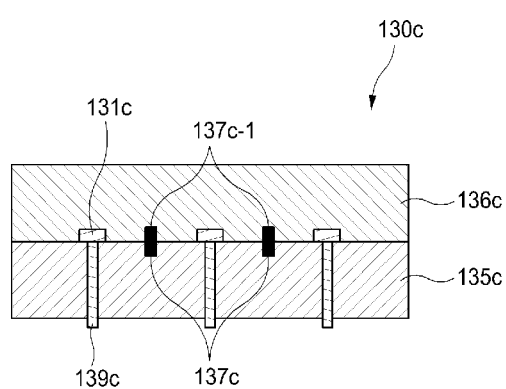
FIG. 6 is a cross-sectional view illustrating the third structure of the electrical stimulation unit constituting the present disclosure.

The electrical stimulation unit 130c of the third type includes a body unit 135c, a mounting unit 136c, and a magnet 137c, as illustrated in FIGS. 5 and 6.

The body unit 135c is detachably attached to the skin of a subject. The body unit 135c includes two or more contact terminals 139c to be in electrical contact with an acupoint area. The contact terminals 139c are in close contact with the skin. The body unit 135c includes the magnet 137c in the upper portion thereof.

The mounting unit 136c includes the electrodes 131c such that the electrodes 113c are exposed on the lower portion thereof. The exposed electrodes 131c and the contact terminals 139c are arranged to be electrically connected to each other in the state in which the body unit 135c and the mounting unit 136c are coupled to each other.

The mounting unit 136c includes a magnet attachment portion 137c-1 at a position corresponding to the magnet 137c of the body unit 135c. The magnet attachment portion 137c-1 is made of a material that forms attractive force with the magnet by magnetic force, such as metal. Accordingly, the body unit 135c and the mounting unit 136c are coupled to each other by magnetic force, and the positions thereof may be aligned by the magnetic force.

Although not illustrated in the drawings, magnets may be provided on both the mounting unit and the body unit. In addition, a magnet attachment portion may be provided in the mounting unit, and a magnet may be provided in the body unit.

Further, although not illustrated in the drawings, in order to improve the coupling force between the body unit and the mounting unit, a protrusion may be formed on the edge of the body unit so as to prevent slipping of the mounting unit.

The magnet 137c and the magnet attachment portion 137c-1 are preferably disposed on the surfaces where the body unit 135c and the mounting unit 136c are to be in contact with each other, and may be disposed inside the body unit 135*c* and the mounting unit 136*c*, respectively.

The electrical stimulation units 130*b* and 130*c* of the second and third types may further include a fixing unit.

The fixing unit is configured to fix the contact terminals 139*b* and 139*c* in the state of being in close contact with the skin of an acupoint area. The fixing unit may be formed in the form of a belt or in the form of a band made of an elastic material.

Figure 7:
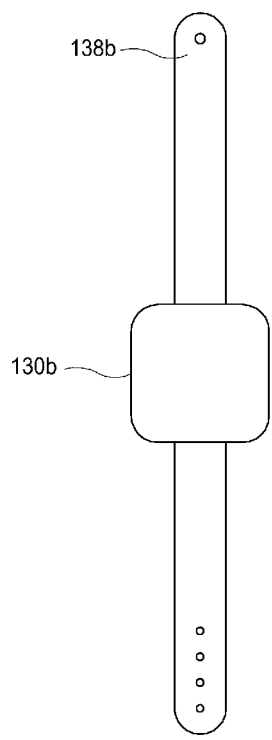
FIG. 7 is a plan view illustrating a belt-shaped fixing unit of the present disclosure.
Figure 8:
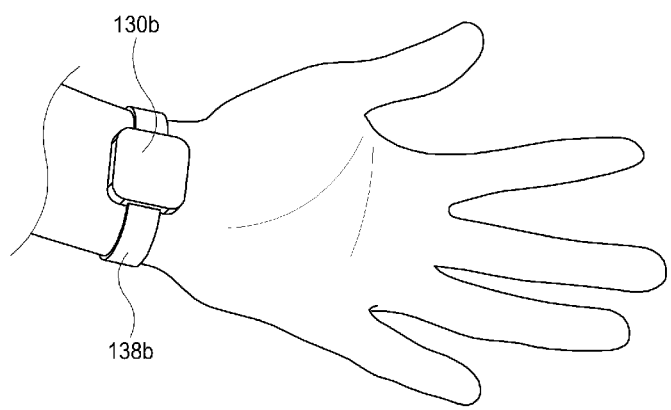
FIG. 8 is a perspective view illustrating the state in which the belt-shaped fixing unit of the present disclosure is worn.

As illustrated in FIG. 7, in the belt-shaped fixing unit 138*b*, belts are disposed on opposite sides of the electrical stimulation unit 130*b*. Thus, the opposite ends of the belts on the opposite sides are connected and fixed to each other like a general watch strap. This fixing unit 138*b* may wrap around a wrist and fix the electrical stimulation unit 130*b* to the wrist, as illustrated in FIG. 8. In addition to the wrist, the electrical stimulation unit may be fixed to a body part around which the fixing unit can be wrapped, such as a forearm, an ankle, or a leg.

Figure 9:
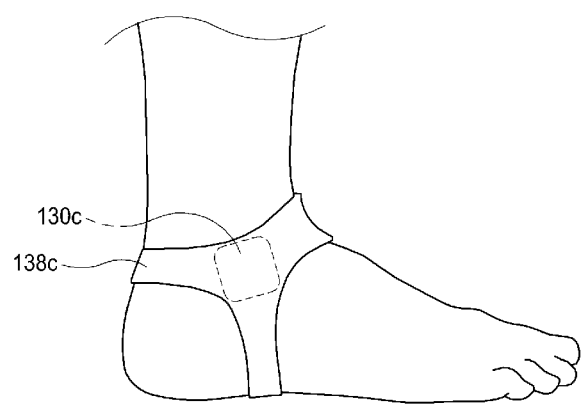
FIG. 9 is a side view illustrating the state in which the electrical stimulation unit is fixed using a band-shaped fixing unit made of an elastic material of the present disclosure.

As illustrated in FIG. 9, an elastic band-shaped fixing unit 138*c* presses the electrical stimulation unit 130*c* against the skin using an elastic force in the state in which the electrical stimulation unit 130*c* is in contact with the skin. Accordingly, the adhesion between the contact terminals of the electrical stimulation unit 130*c* and the skin is improved.

The elastic band-shaped fixing unit 138*c* may fix the electrical stimulation unit to any of various body parts, on which the electrical stimulation unit can be fixed using a band, such as a wrist, a forearm, an ankle, a leg, a foot, the back of a hand, or a head.

The electrical stimulation unit 130 may have two or more electrodes arranged in various ways, and more preferably three or more electrodes. Hereinafter, various arrangement methods of the electrodes will be described.

Figure 10:
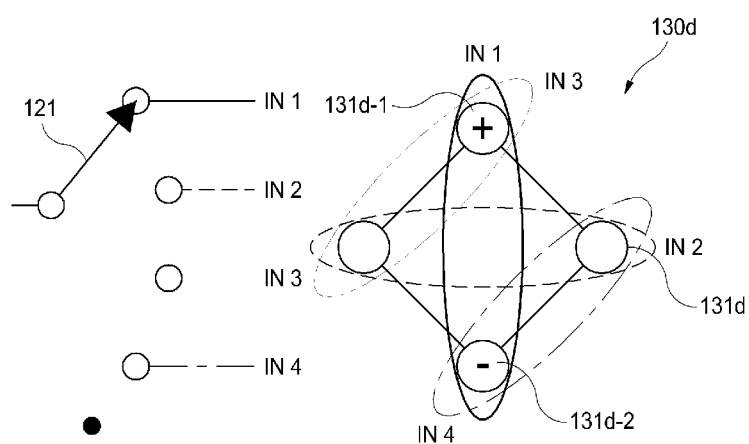
FIG. 10 is a view illustrating a first electrode arrangement method of the present disclosure.

As illustrated in FIG. 10, in an electrical stimulation unit 130*d*, one electrode 131*d* is disposed at each of the top, bottom, left, and right on the drawing. In this case, an anode 131*d*-1 and a cathode 131*d*-2 are respectively applied to two electrodes selected from among the electrodes 131*d* so as to provide electrical stimulation to an acupoint area on which the electrical stimulation unit 130*d* is mounted.

The anode 131*d*-1 and the cathode 131*d*-2 are selected by a switching unit 121 of the first controller 120. The switching unit 121 selects two electrodes from among the plurality of electrodes 131*d*, and the switching unit 121 applies the anode 131*d*-1 to one of the electrodes 131*d*, and applies the cathode 131*d*-2 to another electrode 131*d*. The anode 131*d*-1 and the cathode 131*d*-2 may be variable under the control of the switching unit 121. Accordingly, the position of the acupoint area to which electrical stimulation is provided may be adjusted depending on the positions of the selected anode 131*d*-1 and cathode 131*d*-2.

Figure 11:
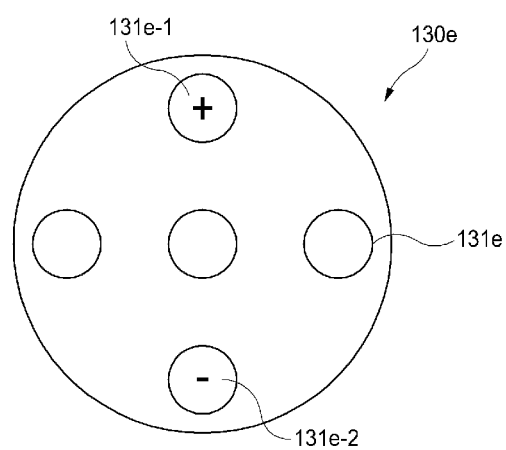
FIG. 11 is a view illustrating a second electrode arrangement method of the present disclosure.

As illustrated in FIG. 11, in an electrical stimulation unit 130*e*, one electrode 131*e* is disposed at the center of the drawing, and one electrode 131*e* is disposed at each of the top, bottom, left, and right on the drawing. In this case, an anode 131*e*-1 and a cathode 131*e*-2 are respectively applied to two electrodes selected from among the electrodes 131*e* so as to provide electrical stimulation to an acupoint area on which the electrical stimulation unit 130*e* is mounted.

The anode 131*e*-1 and the cathode 131*e*-2 may be variable under the control of the switching unit. Accordingly, the position of the acupoint area to which electrical stimulation is provided may be adjusted depending on the positions of the selected anode 131*e*-1 and cathode 131*e*-2.

Figure 12:
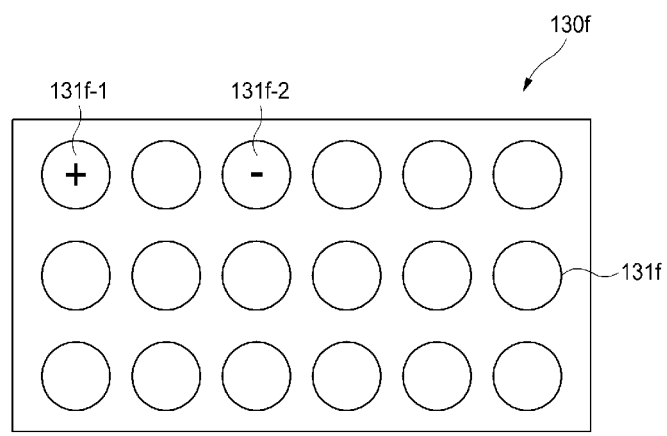
FIG. 12 is a view illustrating a third electrode arrangement method of the present disclosure.

As illustrated in FIG. 12, in an electrical stimulation unit 130*f*, electrodes 131*f* may be arranged in a matrix in an imaginary square. Specifically, the electrodes 131*f* may be arranged in 3 rows and 6 columns. In this case, an anode 131*f*-1 and a cathode 131*f*-2 are respectively applied to two electrodes selected from among the electrodes 131*f* so as to provide electrical stimulation to an acupoint area on which the electrical stimulation unit 130*f* is mounted.

The anode 131*f*-1 and the cathode 131*f*-2 may be variable under the control of the switching unit. Accordingly, the position of the acupoint area to which electrical stimulation is provided may be adjusted depending on the positions of the selected anode 131*f*-1 and cathode 131*f*-2.

Figure 13:
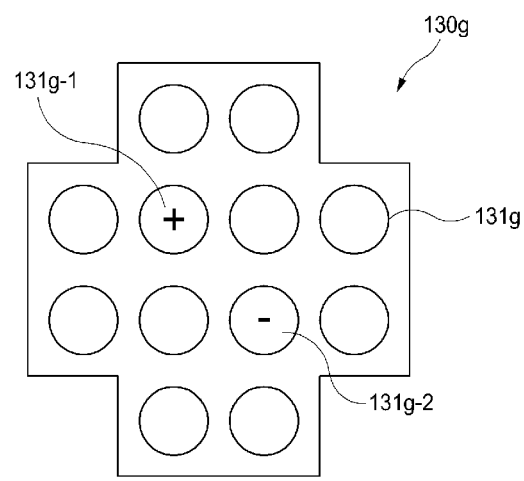
FIG. 13 is a view illustrating a fourth electrode arrangement method of the present disclosure.

As illustrated in FIG. 13, in an electrical stimulation unit 130*g*, electrodes 131*g* may be arranged inside a virtual cross shape. Specifically, among the electrodes 131*g*, four electrodes may be arranged in two rows and two columns in the central area, and two electrodes may be additionally arranged in each of the areas extending upwards, downwards, leftwards, and rightwards from the four electrodes in the central area. In this case, an anode 131*g*-1 and a cathode 131*g*-2 are respectively applied to two electrodes selected from among the electrodes 131*f* so as to provide electrical stimulation to an acupoint area on which the electrical stimulation unit 130*g* is mounted.

The anode 131*g*-1 and the cathode 131*g*-2 may be variable under the control of the switching unit. Accordingly, the position of the acupoint area to which electrical stimulation is provided may be adjusted depending on the positions of the selected anode 131*g*-1 and cathode 131*g*-2.

Figure 14:
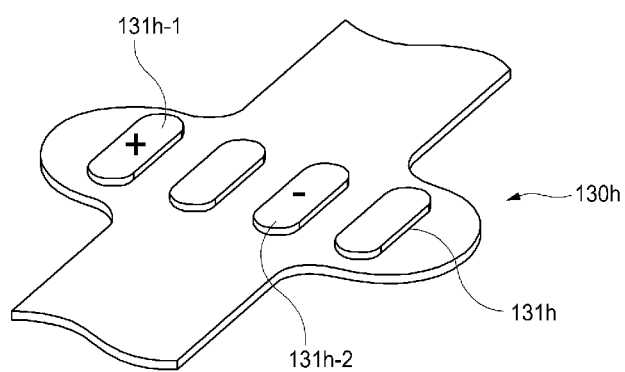
FIG. 14 is a view illustrating a fifth electrode arrangement method of the present disclosure.

As illustrated in FIG. 14, in an electrical stimulation unit 130*h*, electrodes 131*h* are arranged in a line. In this case, an anode 131*h*-1 and a cathode 131*h*-2 are respectively applied to two electrodes selected from among the electrodes 131*h* so as to provide electrical stimulation to an acupoint area on which the electrical stimulation unit 130*h* is mounted.

The anode 131*h*-1 and the cathode 131*h*-2 may be variable under the control of the switching unit. Accordingly, the position of the acupoint area to which electrical stimulation is provided may be adjusted depending on the positions of the selected anode 131*h*-1 and cathode 131*h*-2.

Figure 15:
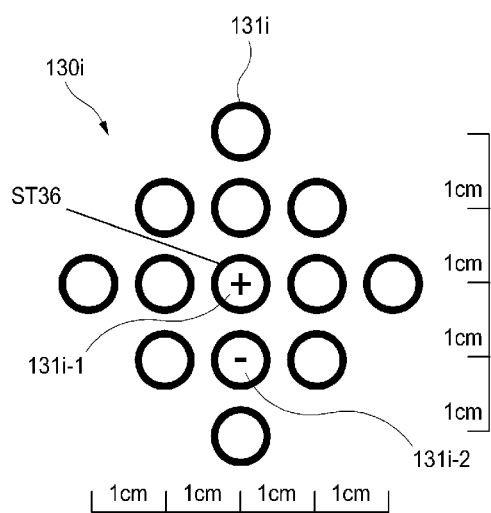
FIG. 15 is a view illustrating a sixth electrode arrangement method of the present disclosure.

As illustrated in FIG. 15, in an electrical stimulation unit 130*i*, electrodes 131*i* may be arranged inside a virtual diamond shape. Specifically, five electrodes 131*i* may be arranged on each of the horizontal and vertical diagonal lines of the virtual diamond shape. In this case, an anode 131*i*-1 and a cathode 131*i*-2 are respectively applied to two electrodes selected from among the electrodes 131*i* so as to provide electrical stimulation to an acupoint area on which the electrical stimulation unit 130*i* is mounted.

The anode 131*i*-1 and the cathode 131*i*-2 may be variable under the control of the switching unit. Accordingly, the position of the acupoint area to which electrical stimulation is provided may be adjusted depending on the positions of the selected anode 131*i*-1 and cathode 131*i*-2.

In the electrode arrangements as described above, the distance between the two selected electrodes to which the anode and the cathode are applied is preferably 5 mm to 30 mm. When the distance between the anode and the cathode is too close, the two electrodes may be recognized as one electrode, and when the distance between the anode and the cathode is too far, there is problem in that the difference between the impedance between the two electrodes and the impedance of a tissue outside the electrodes becomes small and thus a stimulus signal cannot be applied to the gap between the two electrodes.

The electrical stimulation unit 130 of the present disclosure provides electrical stimulation to an acupoint area, in which electrodes to which an anode is applied and electrodes to which a cathode is applied may be disposed in one electrical stimulation unit, and the positions of the anode and the cathode to which power is applied may be selectively determined via the switching unit.

In this case, the first controller 120 may determine the application frequency, the strength, the number of application times, and the intensity of a stimulus signal to be applied to an anode and a cathode, and the positions of the anode and the cathode may be determined depending on a symptom and disease of a subject.

In contrast, the conventional electrical stimulator provides electrical stimulation to the skin, and has features in which an electrical stimulator to which an anode is applied and an electrical stimulator to which a cathode is applied are configured separately, and in which the distance between the cathode and the cathode must be at least 100 mm.

The first biosignal measurement unit 140 measures biosignals of a subject. The biosignals may include an EEG, an EMG, an EOG, a heart rate, a body temperature, or the like of a subject. The measured biosignals are collected by the first controller 120.

The first biosignal measurement unit 140 is provided in the acupoint stimulation device 100 so as to measure the biosignals from the skin at a location where the acupoint stimulation device 100 is mounted. For example, when the acupoint stimulation device is mounted on a wrist, it is possible to measure a heart rate, a body temperature, or the like.

The temperature sensor unit 150 measures the skin temperature of the acupoint of a subject. The measured skin temperature is collected by the first controller 120.

As illustrated in FIG. 2, the heating unit 160 provides heat to a subject to increase the temperature of the deep portion of an acupoint area. In this case, the heating unit 160 receives power from the power supply unit 110. The heating unit 160 may be constituted with an induction coil or an LED.

First, when the heating unit 160 is constituted with an induction coil, the induction coil is disposed in parallel with the skin surface of an acupoint area in the state of being spaced apart from the electrodes 131*a* to form an eddy current in the deep portion of the acupoint area of the subject so as to heat the deep portion.

Next, when the heating unit 160 is constituted with an LED, the LED is disposed between the electrodes 131*a* so as to emit light energy to the deep portion of the acupoint area of the subject so as to heat the deep portion.

Hereinafter, a control method of the first controller 120 will be described with reference to the arrangement of the electrodes 131*i* of the electrical stimulation unit 130*i* illustrated in FIG. 15.

Control method 1) The first controller 120 applies a stimulus signal to an anode 131*i* and a cathode 131*i*-2, which are an electrode pair consisting of two electrodes selected from among the electrodes 131*i*.

Control method 2) The first controller 120 alternately applies a stimulus signal to a plurality of electrode pairs. Here, the term "electrode pair" means an anode and a cathode determined according to the selection of the switching unit. At this time, the positions of the anode and the cathode are variable so that various electrode pairs can be configured.

Accordingly, the electrical stimulation unit 130*i* may stimulate an acupoint and a portion around the acupoint. In addition, even if the user cannot accurately match the center of the electrical stimulation unit 130*i* with the position of the acupoint, the electrical stimulation unit 130*i* may stimulate the acupoint area.

Control method 3) The first controller 120 collects the measured biosignals from the first biosignal measurement unit 140, and calculates a biometric level. The first controller 120 compares the calculated biometric level with a preset target biometric level so as to generate an appropriate stimulus signal.

For example, it is assumed that the higher the biometric level, the more stable the subject is and the higher the biometric level when stimulating an acupoint area in which the electrical stimulation unit is located. When the calculated biometric level is lower than the target biometric level, the first controller 120 generates a stimulus signal for increasing the biometric level and applies the stimulus signal to the electrical stimulation unit 130*i*, and when the calculated biometric level is equal to or higher than the target biometric level, the supply of the stimulus signal to the electrical stimulation unit 130*i* is stopped.

Control method 4) The first controller 120 alternately applies stimulus signals to a plurality of electrode pairs, collects the measured biosignals from the first biosignal measurement unit 140, and then calculates each of biometric levels of each electrode pair. The first controller 120 sets an electrode pair having a relatively superior biometric level among respective biometric levels as a reference electrode pair, and applies a stimulus signal to the reference electrode pair.

The biometric level is calculated as the superior biometric level as the stimulation is provided to a location close to an acupoint. That is, the reference electrode pair provides stimulation at the position closest to the acupoint compared to other electrode pairs. By applying a stimulus signal to the reference electrode pair, the first controller 120 is capable of accurately stimulating the acupoint area, and is capable of improving the acupoint stimulation effect.

Control method 5) The first controller 120 measures the biopotential of each of the electrodes 131*i*, and calculates a biopotential similarity of each of the electrodes 131*i* based on the measured biopotential. The first controller 120 sets an electrode pair having a relatively high similarity in the calculated biopotential as a reference electrode pair, and applies a stimulus signal to the reference electrode pair.

The biopotential similarity is calculated as being higher at a position closer to an acupoint. That is, the reference electrode pair provides stimulation at a position closest to the acupoint compared to other electrode pairs.

Figure 16:
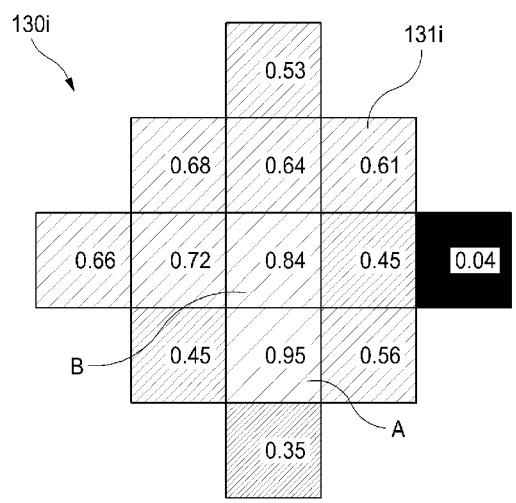
FIG. 16 is a view showing a biopotential similarity of each electrode obtained through an experiment in the sixth electrode arrangement method of the present disclosure.

Referring to FIG. 16, it may be estimated that an acupoint is located between the electrode A having the highest biopotential similarity and the electrode B having the second highest biopotential similarity. Accordingly, the first controller 120 sets the electrode A and the electrode B as a reference electrode pair, and applies a stimulus signal to the reference electrode pair. In this way, it is possible to accurately stimulate an acupoint area and to improve the acupoint stimulation effect.

As a specific example, reference is made to experimental data for comparing potential differences around the foot reflexology acupoint.

Figure 17:
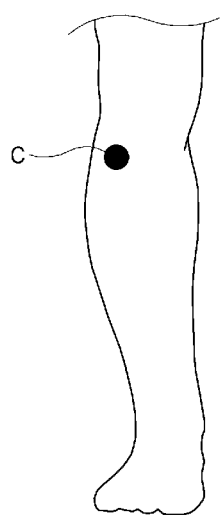
FIG. 17 is a view illustrating the location of a subject's foot reflexology acupoint.

Subjects are 5 persons who are healthy males in their 20s or 30s, have no experience of surgery within 1 year, no experience of taking drugs within 1 month, and have no disease or allergy to metals. As illustrated in FIG. 17, the foot reflexology acupoint C is an outer portion below a knee.

As the acupoint stimulation device, a bioscan (available from TASFO of Korea) and a gold electrode (available from KIOM of Korea) are used, and are placed at the foot reflexology acupoint A.

As illustrated in FIG. 15, the electrodes are arranged radially around the foot reflexology acupoint ST36, and are generally arranged inside the virtual diamond shape.

The biopotential is measured for 30 minutes in this state.

The first controller calculates the biopotential similarity of each electrode based on the measured biopotential, wherein an equation for calculating each biopotential similarity is as follows.

$$S(A, B) = \frac{1}{N}\sum_{i=1}^{N} \Delta_{Ai} * \Delta_{Bi}, \quad A * B = \begin{matrix} 1: A \text{ and } B \text{ has same sign} \\ 0: A \text{ and } B \text{ has different sign} \end{matrix} \quad \text{Equation 1}$$

The biopotential similarity of each electrode calculated by the above equation is shown as illustrated in FIG. 16, and as the biopotential similarity is closer to 1, the conductivity with the surrounding electrodes is higher. From this, the first controller determines that an acupoint exist between the electrode A (0.94) and the electrode B (0.84), each of which has a high biopotential similarity, sets the electrode A and the electrode B as a reference electrode pair, and applies a stimulus signal to the reference electrode pair.

Accordingly, it is possible to accurately provide a stimulus signal to the acupoint area, and to improve the acupoint stimulation effect.

Control method 6) When the skin temperature measured by the temperature sensor unit reaches a set temperature, the first controller 120 performs control such that the supply of the stimulus signal is stopped. Accordingly, it is possible to prevent burn damage caused when the skin is overheated according to the supply of the stimulus signal.

Control method 7) When the skin temperature measured by the temperature sensor unit reaches a set temperature, the first controller 120 performs control such that the power supplied to the heating unit is cut off. This can prevent burn damage caused when power is supplied to the heating unit to overheat the deep portion of the acupoint area and to excessively increase the temperature of the deep portion and the skin temperature of the acupoint area.

As described above, the first controller 120 may control the electrical stimulation unit 130 and the heating unit 160 according to the physical condition of the subject.

The acupoint stimulation device according to the second embodiment is different from that of the first embodiment in that the former further includes a stimulation device communication unit 170 and a user terminal 200, as illustrated in FIG. 1. Hereinafter, components different from those of the first embodiment will be described in detail.

The stimulation device communication unit 170 is provided inside the acupoint stimulation device 100. The stimulation device communication unit 170 is a means for communicating information and signals with the user terminal 200. The stimulation device communication unit 170 transmits a biosignal measured using the first biosignal measurement unit 140 to the user terminal 200, and receives a stimulus signal from the user terminal 200. The received stimulus signal is applied to the electrical stimulation unit 130.

The user terminal 200 is a means that is operable by the user and communicates with the acupoint stimulation device 100, and includes a terminal communication unit 210, a second controller 220, an alarm unit 230, and a storage unit 240, as illustrated in FIG. 1.

The terminal communication unit 210 communicates with the stimulation device communication unit 170 in a wired or wireless manner. The terminal communication unit 210 receives the biosignal from the stimulation device communication unit 170, and transmits a stimulus signal to the stimulation device communication unit 170.

The second controller 220 may generate a stimulus signal according to the biosignal received from the terminal communication unit 210. In addition, the second controller 220 may generate an alarm unit operation signal that controls whether to operate the alarm unit 230. The second controller 220 is included in the controller together with the first controller 120.

The alarm unit 230 provides an alarm according to an alarm time set by a user. In addition, the alarm unit 230 may provide an alarm according to an alarm unit operation signal generated by the second controller 220. The provided alarm may be sensory stimulation such as sound stimulation, brightness stimulation, or tactile stimulation.

The storage unit 240 stores data such as a biosignal received from the terminal communication unit 210 and a stimulus signal and an alarm unit operation signal generated by the second controller 220. Accordingly, the storage unit 240 may store the past history of the subject. In this case, when the subject reuses the acupoint stimulation device, the second controller 220 may generate a stimulus signal and an alarm unit operation signal by referring to the past history of the subject stored in the storage unit 240.

Specifically, a biosignal measured by the first biosignal measurement unit 140 of the acupoint stimulation device 100 and a skin temperature measured by the temperature sensor unit 150 are transmitted to the second controller 220 of the user terminal 200 via the stimulation device communication unit 170. The second controller 220 generates a stimulus signal, a heating unit operation signal, an alarm unit operation signal, or the like with reference to the transmitted signal. The stimulus signal is applied to the electrical stimulation unit 130 of the acupoint stimulation device 100 via the terminal communication unit 210. The heating unit operation signal is applied to the heating unit 160 of the acupoint stimulation device 100 via the terminal communication unit 210. The alarm unit operation signal is applied to the alarm unit 230 of the user terminal 200.

Hereinafter, a control method of the second controller 220 will be described with reference to the arrangement of the electrodes 131$i$ of the electrical stimulation unit 130$i$ illustrated in FIG. 15.

Control method 1) The second controller 220 applies a stimulus signal to an anode 131$i$-1 and a cathode 131$i$-2, which are an electrode pair consisting of two electrodes selected from among the electrodes 131$i$.

Control method 2) The second controller 220 alternately applies a stimulus signal to a plurality of electrode pairs. Here, the term "electrode pair" means an anode and a cathode determined according to the selection of the switching unit. At this time, the positions of the anode and the cathode are variable so that various electrode pairs can be configured.

Accordingly, the electrical stimulation unit 130$i$ may stimulate an acupoint and a portion around the acupoint. In addition, even if the user cannot accurately match the center of the electrical stimulation unit 130$i$ with the position of the acupoint, the electrical stimulation unit 130$i$ may stimulate the acupoint area.

Control method 3) The second controller 220 collects the measured biosignals from the first biosignal measurement unit 140, and calculates a biometric level. The second controller 220 compares the calculated biometric level with a preset target biometric level so as to generate an appropriate stimulus signal.

For example, it is assumed that the higher the biometric level, the more stable the subject is and the higher the biometric level when stimulating an acupoint area in which the electrical stimulation unit is located. When the calculated biometric level is lower than the target biometric level, the second controller 220 generates a stimulus signal for increasing the biometric level and applies the stimulus signal to the electrical stimulation unit 130$i$, and when the calculated biometric level is equal to or higher than the target biometric level, the supply of the stimulus signal to the electrical stimulation unit 130$i$ is stopped.

Control method 4) The second controller 220 alternately applies stimulus signals to a plurality of electrode pairs, collects the measured biosignals from the first biosignal measurement unit 140, and then calculates each of biometric levels of each electrode pair. The second controller 220 sets an electrode pair having a relatively superior biometric level among respective biometric levels as a reference electrode pair, and applies a stimulus signal to the reference electrode pair.

The biometric level is calculated as the superior biometric level as the stimulation is provided to a location close to an acupoint. That is, the reference electrode pair provides stimulation at the position closest to the acupoint compared to other electrode pairs. By applying a stimulus signal to the reference electrode pair, the second controller 220 is capable of accurately stimulating the acupoint area, and is capable of improving the acupoint stimulation effect.

Control method 5) The second controller 220 measures the biopotential of each of the electrodes 131$i$, and calculates a biopotential similarity of each of the electrodes 131$i$ based on the measured biopotential. The second controller 220 sets an electrode pair having a relatively high similarity in the calculated biopotential as a reference electrode pair, and applies a stimulus signal to the reference electrode pair.

The biopotential similarity is calculated as being higher at a position closer to an acupoint. That is, the reference electrode pair provides stimulation at a position closest to the acupoint compared to other electrode pairs.

Referring to FIG. 16, it may be estimated that an acupoint is located between the electrode A having the highest biopotential similarity and the electrode B having the second highest biopotential similarity. Accordingly, the second controller 220 sets the electrode A and the electrode B as a reference electrode pair, and applies a stimulus signal to the reference electrode pair. In this way, it is possible to accurately stimulate an acupoint area and to improve the acupoint stimulation effect.

Control method 6) When the skin temperature measured by the temperature sensor unit reaches a set temperature, the second controller 220 performs control such that the supply of the stimulus signal is stopped. Accordingly, it is possible to prevent burn damage caused when the skin is overheated according to the supply of the stimulus signal.

Control method 7) When the skin temperature measured by the temperature sensor unit reaches a set temperature, the second controller 220 performs control such that the power supplied to the heating unit is cut off. This can prevent burn damage caused when power is supplied to the heating unit to overheat the deep portion of the acupoint area and to excessively increase the temperature of the deep portion and the skin temperature of the acupoint area.

As described above, the second controller 220 may control the electrical stimulation unit 130 and the heating unit 160 according to the physical condition of the subject.

In the acupoint stimulation device according to the second embodiment, the controller may include a first controller 120 and a second controller 220, and may optionally include the first controller 120.

When the acupoint stimulation device according to the second embodiment includes the first controller 120 and the second controller 220, the second controller 220 processes some of the control methods of the second controller 220, and the first controller 12 may process the remaining ones of the control methods.

When the acupoint stimulation device according to the second embodiment does not include the first controller 120, the second controller 220 processes all the above-described control methods of the second controller 220.

Meanwhile, the user terminal 200 may display biometric information, such as the collected biosignals and skin temperatures, to the user. In addition, the user terminal 200 may directly receive information for generating a stimulus signal, which is input by a user.

The acupoint stimulation device according to the third embodiment is different from that of the second embodiment in that the former further includes a biometric information collector 300, as illustrated in FIG. 1. Hereinafter, components different from those of the second embodiment will be described in detail.

The biometric information collector 300 is provided to be spaced apart from the electrical stimulation unit 130, and includes a second biosignal measurement unit 310 and a collector communication unit 320.

The second biosignal measurement unit 310 measures a biosignal of the subject from a position spaced apart from the acupoint stimulation device 100. For example, when the acupoint stimulation device 100 is mounted on a wrist and the biosignal collector is mounted on the forehead, the first biosignal measurement unit 140 located on the wrist measures a pulse rate, and the second biosignal measurement unit 310 located on the forehead measures an EEG. At this time, the acupoint stimulation device 100 provides stimulation to the wrist. The second biosignal measurement unit 310 is included in the biosignal measurement unit together with the first biosignal measurement unit 140.

The acupoint stimulation device according to the third embodiment may optionally include a first biosignal measurement unit 140 depending on a position at which a biosignal is measured, a position at which the acupoint stimulation device 100 is mounted, and a position where the biosignal collector 300 is mounted.

When the acupoint stimulation device according to the third embodiment includes the first biosignal measurement unit 140, a biosignal may be measured from a body part to which stimulation is provided. For example, when the acupoint stimulation device 100 is mounted on the wrist, the first biosignal measurement unit 140 measures a pulse rate and a body temperature from the wrist, and the electrical stimulation unit 130 provides stimulation to the wrist.

When the acupoint stimulation device according to the third embodiment does not include the first biosignal measurement unit, a biosignal may be measured from a body part spaced apart from the body part to which stimulation is provided. For example, when the acupoint stimulation device 100 is mounted on the wrist and the biosignal collector 300 is mounted on the forehead, the second biosignal measurement unit 310 measures an EEG from the forehead, and the electrical stimulation unit 130 provides stimulation to the wrist.

The collector communication unit 320 communicates with the terminal communication unit 210 in a wired or wireless manner. The collector communication unit 320 transmits the biosignal measured by the second biosignal measurement unit 310 to the terminal communication unit 210 of the user terminal 200.

The terminal communication unit 210 communicates with the stimulation device communication unit 170 and the collector communication unit 320.

Hereinafter, a control method of the second controller 220 will be described with reference to the arrangement of the electrodes 131*i* of the electrical stimulation unit 130*i* illustrated in FIG. 15.

Control method 1) The second controller 220 applies a stimulus signal to an anode 131*i*-1 and a cathode 131*i*-2, which are an electrode pair consisting of two electrodes selected from among the electrodes 131*i*.

Control method 2) The second controller 220 alternately applies a stimulus signal to a plurality of electrode pairs. Here, the term "electrode pair" means an anode and a cathode determined according to the selection of the switching unit. At this time, the positions of the anode and the cathode are variable so that various electrode pairs can be configured.

Accordingly, the electrical stimulation unit 130*i* may stimulate an acupoint and a portion around the acupoint. In addition, even if the user cannot accurately match the center of the electrical stimulation unit 130*i* with the position of the acupoint, the electrical stimulation unit 130*i* may stimulate the acupoint area.

Control method 3) The second controller 220 collects measured biosignals from at least one of the first biosignal measurement unit 140 and the second biosignal measurement unit 310, and calculates a biometric level. The second controller 220 compares the calculated biometric level with a preset target biometric level so as to generate an appropriate stimulus signal.

For example, it is assumed that the higher the biometric level, the more stable the subject is and the higher the biometric level when stimulating an acupoint area in which the electrical stimulation unit is located. When the calculated biometric level is lower than the target biometric level, the second controller 220 generates a stimulus signal for increasing the biometric level and applies the stimulus signal to the electrical stimulation unit 130*i*, and when the calculated biometric level is equal to or higher than the target biometric level, the supply of the stimulus signal to the electrical stimulation unit 130*i* is stopped.

Control method 4) The second controller 220 alternately applies stimulus signals to a plurality of electrode pairs, collects the measured biosignals from at least one the first biosignal measurement unit 140 and the second biosignal measurement unit 310, and then calculates each of biometric levels of each electrode pair. The second controller 220 sets an electrode pair having a relatively superior biometric level among respective biometric levels as a reference electrode pair, and applies a stimulus signal to the reference electrode pair.

The biometric level is calculated as the superior biometric level as the stimulation is provided to a location close to an acupoint. That is, the reference electrode pair provides stimulation at the position closest to the acupoint compared to other electrode pairs. By applying a stimulus signal to the reference electrode pair, the second controller 220 is capable of accurately stimulating the acupoint area, and is capable of improving the acupoint stimulation effect.

Control method 5) The second controller 220 measures the biopotential of each of the electrodes 131*i*, and calculates a biopotential similarity of each of the electrodes 131*i* based on the measured biopotential. The second controller 220 sets an electrode pair having a relatively high similarity in the calculated biopotential as a reference electrode pair, and applies a stimulus signal to the reference electrode pair.

The biopotential similarity is calculated as being higher at a position closer to an acupoint. That is, the reference electrode pair provides stimulation at a position closest to the acupoint compared to other electrode pairs.

Referring to FIG. 16, it may be estimated that an acupoint is located between the electrode A having the highest biopotential similarity and the electrode B having the second highest biopotential similarity. Accordingly, the second controller 220 sets the electrode A and the electrode B as a reference electrode pair, and applies a stimulus signal to the reference electrode pair. In this way, it is possible to accurately stimulate an acupoint area and to improve the acupoint stimulation effect.

Control method 6) When the skin temperature measured by the temperature sensor unit reaches a set temperature, the second controller 220 performs control such that the supply of the stimulus signal is stopped. Accordingly, it is possible to prevent burn damage caused when the skin is heated according to the supply of the stimulus signal.

Control method 7) When the skin temperature measured by the temperature sensor unit reaches a set temperature, the second controller 220 performs control such that the power supplied to the heating unit is cut off. This can prevent burn damage caused when power is supplied to the heating unit to overheat the deep portion of the acupoint portion and to excessively increase the temperature of the deep portion and the skin temperature of the acupoint area.

As described above, the second controller 220 may control the electrical stimulation unit 130 and the heating unit 160 according to the physical condition of the subject.

In the acupoint stimulation device according to the third embodiment, the controller may include a first controller 120 and a second controller 220, and may optionally include the first controller 120 and the second controller 220.

When the acupoint stimulation device according to the third embodiment includes the first controller 120 and the second controller 220, the second controller 220 processes some of the control methods of the second controller 220, and the first controller 12 may process the remaining ones of the control methods.

When the acupoint stimulation device according to the third embodiment includes only the first controller 120, the first controller 120 processes all the above-described control methods of the second controller 220.

When the acupoint stimulation device according to the third embodiment includes only the second controller 220, the second controller 220 processes all the above-described control methods of the second controller 220.

Hereinafter, two types of acupoint stimulation methods using the acupoint stimulation device of the present disclosure will be described. An acupoint stimulation method of the present disclosure may be performed using the acupoint stimulation device of the first to third embodiments described above.

Figure 18:
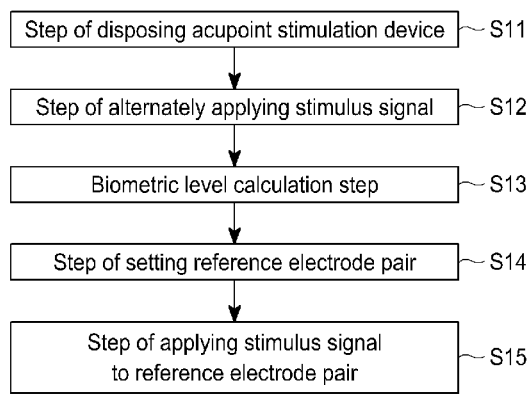
FIG. 18 is a view illustrating a first acupoint stimulation method of the present disclosure.

As illustrated in FIG. 18, the first acupoint stimulation method includes the following steps.

In a step of disposing an acupoint stimulation device (S11), the acupoint stimulation device is disposed on an acupoint area to be stimulated of the subject. Specifically, the acupoint stimulation device is placed in an area that is expected to be an acupoint of the subject.

In a step of alternatively applying a stimulus signal (S12), a stimulus signal is alternately applied to respective electrode pairs each consisting of two selected electrodes.

In a biometric level calculation step (S13), each biometric level corresponding to each electrode pair is calculated from a biosignal measured along each electrode pair to which the stimulus signal is applied.

In a step of setting a reference electrode pair (S14), an electrode pair having a relatively superior biometric level among the respective calculated biometric levels is set as the reference electrode pair.

In a step of applying a stimulus signal to the reference electrode pair (S15), a stimulus signal is applied to the reference electrode pair.

Figure 19:
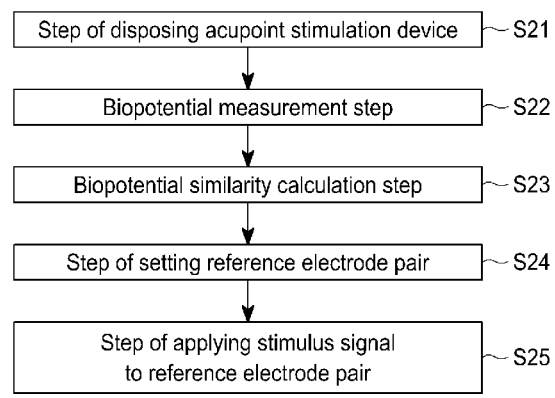
FIG. 19 is a view illustrating a second acupoint stimulation method of the present disclosure.

As illustrated in FIG. 19, a second acupoint stimulation method includes the following steps.

In a step of disposing an acupoint stimulation device (S21), the acupoint stimulation device is disposed on an acupoint area to be stimulated of the subject. Specifically, the acupoint stimulation device is placed in an area that is expected to be an acupoint of the subject.

In a biopotential measurement step (S22), the biopotential of each of the electrodes provided in the acupoint stimulation device is measured.

In a biopotential similarity calculation step (S23), the biopotential similarity of each of the electrodes is calculated based on the measured biopotential.

In a step of setting a reference electrode (S24), an electrode pair consisting of two electrodes and having a relatively high calculated biopotential similarity is set as a reference electrode pair.

In a step of applying a stimulus signal to the reference electrode pair (S25), a stimulus signal is applied to the reference electrode pair.

Hereinafter, a sleep management device using the acupoint stimulation device of the present disclosure will be described in detail. The sleep management device of the present disclosure shares the above-described control methods of the acupoint stimulation device, and further includes a control method for managing sleep. In addition, for convenience of description, the above-described first and second controllers 120 and 220 are collectively referred to as a controller, and the above-described first and second biosignal measurement units 140 and 310 are collectively referred to as a biosignal measurement unit.

The controller generates a stimulus signal that induces a subject to a desired sleep stage according to biosignals collected from the biosignal measurement unit. Specifically, the controller determines the sleep stage of the subject from the biological signals, and controls whether to apply a stimulus signal to be applied to the electrodes, a stimulation frequency, stimulation intensity, and the number of stimulations depending on the determined sleep stage. The controller may apply a stimulus signal to the electrodes disposed on an acupoint area that induce the subject to a desired sleep stage.

Hereinafter, various sleep management control methods of the controller depending on a sleep stage will be described.

For convenience of description, the sleeping stage of a subject is divided into an awakening step, a shallow sleep step, and a deep sleep step. In the awakening step, the subject is in the state in which the subject is awake, in the shallow sleep phase, the subject is in the sleep state in which the subject enters sleep or dreams, and in the deep sleep step, the subject is in the sleep state deeper than that in the shallow sleep step.

1) When the sleep stage of the subject corresponds to the awakening step, the controller applies a stimulus signal to the electrodes disposed on the acupoint area so as to stimulate the acupoint area that induce sleep of a subject.

As a result, it is possible to induce a subject who starts sleeping or a subject who awakens during sleep, which is effective in treating insomnia of the subject.

2) When the subject's sleep stage corresponds to the shallow sleep step, the controller applies a stimulus signal to the electrodes disposed in the corresponding acupoint area so as to stimulate the acupoint area that induces the subject to the deep sleep step.

As a result, it is possible to induce a subject who is continuously in the shallow sleep step and cannot enter the deep sleep step to sleep deeply so that the subject may enter the deep sleep step.

3) The controller may generate a stimulus signal to prevent the subject's sleep step from being switched to the deep sleep step for a predetermined time before a set alarm time. Specifically, the controller may apply a stimulus signal for maintaining the shallow sleep step to the subject or may stop the supply of the stimulus signal so as to maintain the shallow sleep step of the subject. In addition, when the subject is in the deep sleep step for a predetermined time before the set alarm time, the controller may apply a stimulus signal to the subject to induce the subject to the shallow sleep step.

In general, in the case of waking up in the shallow sleep step, the subject may be awakened comfortably. Therefore, by inducing the subject to the shallow sleep step before the set alarm time, it is possible to help the subject to wake up comfortably.

4) When the sleep stage reaches an abnormal sleep state, the controller controls the electrical stimulation unit to induce the subject to the awakening step or operates the alarm unit.

For example, a stimulus signal is applied to the acupoint area that induces the subject to the awakening step, or an alarm is operated.

The abnormal sleep state is the state in which a biosignal is out of a predetermined range from a set reference value. Here, the reference value refers to a biosignal value in the state in which the subject is stable, and when the biosignal value is out of a predetermined range from the reference value, it becomes an unstable state. For example, the abnormal sleep state is an unstable state, such as the state in which a subject has a bad dream or the state in which the subject has a nightmare.

Specifically, the abnormal sleep state is the state in which an amplitude or pattern of a specific frequency band in the collected biosignals is out of a predetermined range from the reference value. With reference to, for example, an EEG, when the amplitude in a specific frequency band (alpha wave or delta wave) increases abnormally from the reference value in the shallow sleep step, it may be determined as an abnormal sleep state.

When a subject is in an unstable state, by inducing the subject from the abnormal sleep state to the awakening stage, the subject may be awakened to escape from a bad dream or the state in which the subject has a nightmare.

5) After the alarm time, when the subject is determined to be in the sleep stage, the controller applies a stimulus signal to the acupoint area that induces the subject to the awakening step or operates the alarm unit. As a result, after the alarm, the subject who has entered the sleep stage is awakened so that it is possible to prevent the subject from excessive oversleeping.

The sleep management device is capable of stimulating spiritual gate acupoint, median nerve, or the like so as to induce the subject to sleep stage.

Figure 20:
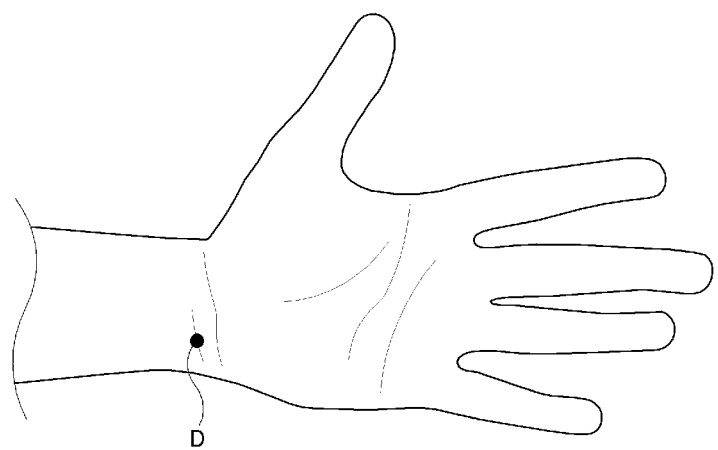
FIG. 20 is a view illustrating the location of a subject's spiritual gate acupoint.
Figure 21:
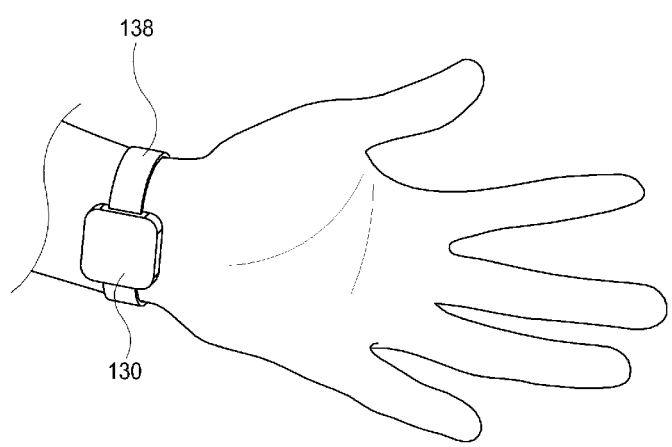
FIG. 21 is a view illustrating the state in which an electrical stimulation unit is disposed on a subject's spiritual gate acupoint.

As illustrated in FIG. 20, the spiritual gate acupoint D is a concave portion oriented toward the little finger from the center of the wrist on the palm side. The spiritual gate acupoint D is responsible for mood, and stimulating the spiritual gate acupoint D is effective for nervous breakdown, heart pain, schizophrenia, heart attack, forgetfulness, insomnia, or the like. From this, as illustrated in FIG. 21, when the sleep management device is mounted on the wrist such that the electrical stimulation unit 130 is located on the spiritual gate acupoint D, it is possible to obtain stress relief and insomnia treatment effects by stimulating the spiritual gate acupoint D depending on the sleep stage.

Figure 22:
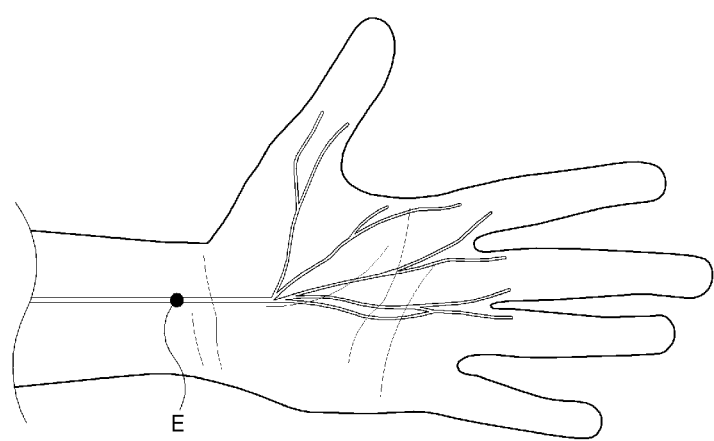
FIG. 22 is a view illustrating the location of a subject's median nerve.

As illustrated in FIG. 22, the median nerve E is one of the peripheral nerves of the arm extending from the upper arm to the hand through the carpal tunnel. Stimulating the C-fiber in the median nerve E can activate the parasympathetic nerve to relieve stress. From this, as illustrated in FIG. 8, when the sleep management device is mounted on the wrist such that the electrical stimulation unit 130b is positioned on the median nerve E, it is possible to control sleep by stimulating the median nerve E depending on the sleep stage to relieve stress of the subject.

Hereinafter, a sleep management method using the sleep management device of the present disclosure will be described step by step.

First, in a step of measuring a biosignal, the sleep management device is disposed at an expected acupoint area of the object, and a biosignal of the subject is measured by the biosignal measurement unit.

In the step of determining a sleep stage, the sleep stage of the subject is determined from the measured biometric signal.

In a stimulus signal generation step, an appropriate stimulus signal is generated depending the determined sleep stage. In this case, a stimulus signal is generated in consideration of whether to apply a stimulus signal, a stimulation frequency, a stimulation intensity, the number of stimulations, or the like.

In a stimulus signal application step, the generated stimulus signal is applied to the electrodes disposed on the acupoint area. Thereby, stimulation can be provided to the acupoint area of the subject.

Hereinafter, a blood pressure adjustment device using the acupoint stimulation device of the present disclosure will be described in detail. The blood pressure adjustment device of the present disclosure shares the above-described control methods of the acupoint stimulation device, and further includes a control method for blood pressure adjustment. In addition, for convenience of description, the above-described first and second controllers 120 and 220 are collectively referred to as a controller, and the above-described first and second biosignal measurement units 140 and 310 are collectively referred to as a biosignal measurement unit.

The controller generates a stimulus signal that adjust the blood pressure of a subject according to biosignals collected from the biosignal measurement unit. Specifically, the controller calculates a stress index or an autonomic nervous system state index of the subject from the biosignals, and controls whether to apply a stimulus signal applied to the electrodes, stimulation frequency, stimulation intensity, the number of stimulations, or the like according to the calculated stress index or autonomic nervous system state index. The controller may apply the stimulus signal to the electrodes disposed on an acupoint area that induces a decrease in blood pressure or stress relief of the subject.

The biosignal measurement unit measures a biosignal of a subject and measures a biosignal for blood pressure adjustment.

The biosignals measured by the biosignal measurement unit preferably include at least one of a blood pressure, an R-R interval, an electroencephalogram (EEG), a heart rate, an electrocardiogram (ECG), a photoplethysmogram (PPG), an oxygen saturation ($SpO_2$), an EOG, and a body temperature.

Hereinafter, a control method of the controller for adjusting blood pressure using a biosignal measured by the biosignal measurement unit will be described.

1) Blood Pressure Control According to Blood Pressure Measurement

The controller measures blood pressure from the biosignal measurement unit. When the measured blood pressure is out of a predetermined range from the set reference value, a stimulus signal is applied to electrodes that stimulate an acupoint area for adjusting the blood pressure of a subject. When the measured blood pressure returns to the predetermined range from the set reference value, the supply of the stimulus signal is stopped.

2) Blood Pressure Adjustment According to Estimated Blood Pressure Using Photoplethysmogram (PPG)

Figure 23:
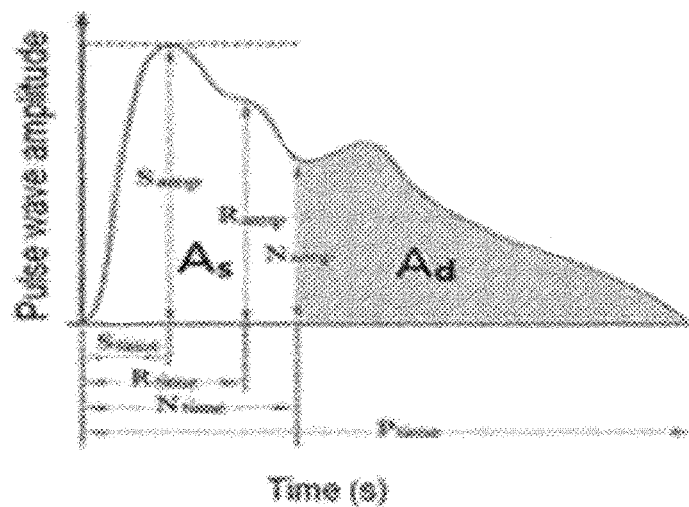
FIG. 23 is a graph showing the pulse wave amplitude of PPG (Photoplethysmogram) over time.

A photoplethysmogram (PPG) is a pulse wave measured using light. As shown in FIG. 23, $S_{amp}$ represents a contraction peak amplitude, Ramp represents a reflection peak amplitude, $N_{amp}$ represents a notch peak amplitude, $S_{time}$ represents a contraction peak time, $R_{time}$ represents a reflection peak time, $N_{time}$ represents a notch amplitude time, $P_{time}$ represents the total time, $A_s$ represents a systolic area before $N_{time}$, and $A_d$ represents a diastolic are after $N_{time}$.

An equation for calculating blood pressure using the parameters collected from the pulse wave of the PPG is as follows.

$$SBP = \frac{1 + \frac{N_{amp}}{S_{amp}}}{\frac{S_{amp}}{N_{amp}}} A_s \qquad \text{Equation 2}$$

$$DBP = \frac{1 + \frac{N_{amp}}{S_{amp}}}{\frac{S_{amp}}{N_{amp}}} A_d$$

In Equation 2 above, SBP represents a systolic blood pressure, and DBP represents a diastolic blood pressure. It is possible to estimate blood pressure by calculating the values of SBP and DBP by substituting parameter values collected from the PPG pulse wave in Equation 2 above, and the SBP and DBP are defined as estimated blood pressure indices, which can be used to estimate the blood pressure of the subject.

Accordingly, the controller extracts parameters including a contraction peak amplitude ($S_{amp}$), a notch peak amplitude ($N_{amp}$), a systolic area ($A_s$), and a diastolic area ($A_d$) from a photoplethysmogram (PPG) measured using the biosignal measurement unit. The extracted parameters are substituted into Equation 2 to calculate the SBP and the DBP, which are blood pressure estimation indices. When the calculated blood pressure estimation indices are out of a predetermined range from the set reference value, a stimulus signal is applied to electrodes that stimulate an acupoint area that adjusts the blood pressure of the subject. When the blood pressure estimation indices reach the predetermined range from the set reference value, the supply of the stimulus signal is stopped.

Figure 24:
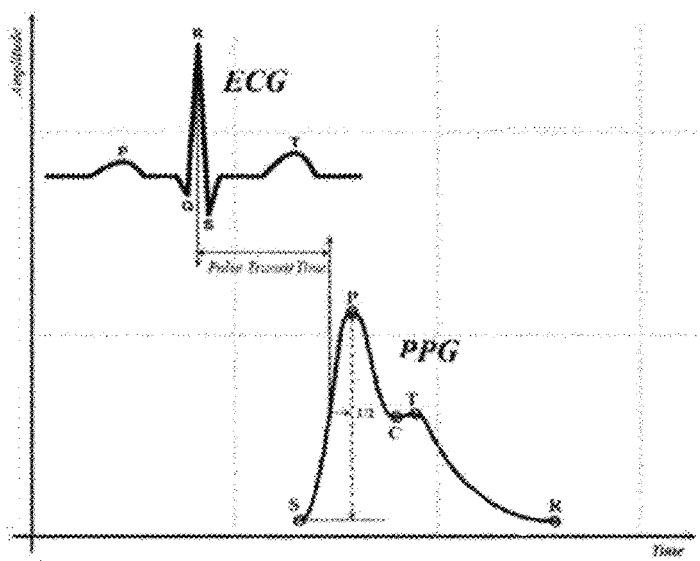
FIG. 24 is a graph showing the amplitude of ECG (Electrocardiogram) and PPG (Photoplethysmogram) over time.

3) Blood Pressure Adjustment According to Estimated Blood Pressure Using ECG and PPG The blood ejected when the heart contracts is delivered to the peripheral blood vessels through an aorta. As shown in FIG. 24, when the heart contracts, the ECG has an amplitude at point R, and the PPG has an amplitude at point P. The PTT signal indicates the time required until the blood ejected from the heart reaches the peripheral blood vessels, that is, the time to the time point at which the blood volume flows into the heart, rather than the time to the time point at which the blood volume of the peripheral blood vessels is maximized. From this, the PTT is defined as a time until a time point having an intermediate value from the time point R of the ECG to the time point P of the PPG.

Since there is a characteristic that the PTT decreases when the blood pressure increases, an equation for calculating the blood pressure using the PTT is as follows.

$$SBP = m_s \frac{1}{PTT} + q_s$$
$$DBP = m_d \frac{1}{PTT} + q_d$$

Equation 3

In Equation 3 above, SBP represents a systolic blood pressure, DBP represents a diastolic blood pressure, and $m_s$, $q_s$, $m_d$, and $q_d$ are coefficients. It is possible to estimate the blood pressure by calculating the values of SBP and DBP by substituting the value of PPT in Equation 3 above, and the SBP and DBP are defined as estimated blood pressure indices, which can be used to estimate the blood pressure of the subject.

Therefore, from the time point that is the point R of the ECG and the time point having the intermediate value between the point S and the point P of the PPG, the controller extracts PTT, which is the distance between the two time points. The extracted PTT is substituted in Equation 3 so as to calculate SBP and DBP, which are blood pressure estimation indices. When the calculated blood pressure estimation indices are out of a predetermined range from the set reference value, a stimulus signal is applied to electrodes that stimulate an acupoint area that adjusts the blood pressure of the subject. When the blood pressure estimation indices reach the predetermined range from the set reference value, the supply of the stimulus signal is stopped.

4) Blood Pressure Control According to Blood Pressure Fluctuation Estimation Index Estimated Using Stress When stress increases, the secretion of cortisol, which is a stress-related hormone, from the adrenal glands increases. Increased secretion of cortisol causes blood pressure to rise. In this case, since it is possible to estimate the amount of secretion of cortisol using the R-R interval, it is possible to estimate an increase in stress from the R-R interval value by linking the R-R interval value and the stress index. Since the increase in stress is a factor that increases blood pressure, it can be estimated the blood pressure will increase when the stress index increases.

The controller calculates a stress index that is a blood pressure fluctuation estimation index, from which a fluctuation in blood pressure can be estimated, by linking the R-R interval value measured from the biosignal measurement unit with stress. When the calculated blood pressure fluctuation estimation index is out of a predetermined range from a set reference value, a stimulus signal is applied to electrodes that stimulate an acupoint area that adjusts the blood pressure of the subject. When the blood pressure fluctuation estimation index reaches the predetermined range from the set reference value, the supply of the stimulus signal is stopped.

In addition, when a sudden stress situation is caused by internal or external factors while the biosignal measurement unit is measuring the R-R interval value in real time, the controller monitors a sudden blood pressure fluctuation, and when a fluctuation in the blood pressure of the subject occurs, the controller stimulates an acupoint area that controls the blood pressure of the subject so as to appropriately adjust the blood pressure of the subject.

5) Blood Pressure Adjustment According to Blood Pressure Fluctuation Estimation Index Estimated Using EEG and Heart Rate Regarding the correlation between an EEG and sympathetic/parasympathetic nerves, theta waves (6 Hz to 8 Hz) of the EEG are related to the activity of parasympathetic nerves, and Alpha waves (8 Hz to 10 Hz) are related to the activity of sympathetic nerves.

Regarding the correlation between a heart rate and sympathetic/parasympathetic nerves, a high frequency (HF) of heart rate variability (HRV) reflects the activity of parasympathetic nerves, and a low frequency of HRV reflects the activity of sympathetic nerves.

From this, an increase in theta waves of the EEG correlates with an increase in the HF of the HRV, and an increase in alpha waves of the EEG correlates with a decrease in the LF of the HRV.

Accordingly, by measuring the EEG and HRV, it is possible to determine a response of an autonomic nervous system including sympathetic/parasympathetic nerves. It can be estimated that activation of parasympathetic nerves in an autonomic nervous system affects the heart rate and increases the blood pressure. Accordingly, it is possible to estimate the activity of sympathetic/parasympathetic nerves through an EEG and a heart rate, and from this, it is possible to estimate a stress index and an autonomic nervous system state index so as to estimate an increase in blood pressure.

The controller extracts the amount of increase or decrease in alpha and theta waves from the EEG measured using the biosignal measurement unit, and extracts the amount of increase or decrease in HF that reflects the activity of parasympathetic nerves and the amount of increase or decrease in LF that reflects the activity of sympathetic nerves from the HRV measured using the biosignal measurement unit. From the extracted amount of increase or decrease in alpha and theta waves and the extracted amount of increase or decrease in HF and LF, a stress index or an autonomic nervous system state index, which is an index for estimating a fluctuation in blood pressure, is calculated. When the calculated blood pressure fluctuation estimation index is out of a predetermined range from a set reference value, a stimulus signal is applied to electrodes that stimulate an acupoint area that adjusts the blood pressure of the subject. When the blood pressure fluctuation estimation index reaches the predetermined range from the set reference value, the supply of the stimulus signal is stopped.

Blood pressure estimation indices are indices used for estimating blood pressure from biosignals other than blood pressure itself, and includes systolic blood pressure (SBP), diastolic blood pressure (DBP), and the like, and blood pressure fluctuation estimation indices are indices used for estimating a fluctuation in blood pressure from biosignals other than blood pressure itself, and include a stress index, an autonomic nervous system state index, and the like.

In addition to the above-described blood pressure measurement, blood pressure estimation, and blood pressure fluctuation estimation methods, it is possible to adjust blood pressure using a method of estimating blood pressure or estimating a fluctuation in blood pressure from various biological signals.

In addition, in the description of the control method described above, the "reference value" is an intermediate value of a normal blood pressure range of a subject having normal blood pressure, and when blood pressure is out of a predetermined range from the reference value, it means that the blood pressure is in a high blood pressure state or a low blood pressure state. In this case, the abnormal state is the state in which a subject's stress is high, or the subject's blood pressure is out of a normal range, that is, in a high blood pressure state or a low blood pressure state.

For example, in the case of a hypertensive patient, when the measured blood pressure exceeds a predetermined range from a set reference value, it means that the blood pressure has been increased. Thus, the controller stimulates an acupoint area that lowers the blood pressure or relieves stress so as to lower the blood pressure. In addition, when the blood pressure estimation index of a hypertensive patient exceeds a predetermined range from a set reference value, it is estimated that the blood pressure will increase. Thus, the controller may stimulate an acupoint area that lowers the blood pressure or relieves stress so as to prevent the blood pressure from increasing.

In order to lower blood pressure or relieve stress, it is possible to stimulate the spiritual gate acupoint or the median nerve.

As illustrated in FIG. 20, the spiritual gate acupoint D is a concave portion oriented toward the little finger from the center of the wrist on the palm side. The spiritual gate acupoint D is responsible for mood, and stimulating the spiritual gate acupoint D is effective for nervous breakdown, heart pain, schizophrenia, heart attack, forgetfulness, insomnia, or the like. From this, as illustrated in FIG. 21, when the blood pressure adjustment device is mounted on a wrist such that the electrical stimulation unit 130 is located on the spiritual gate acupoint D, it is possible to adjust the blood pressure by stimulating the spiritual gate acupoint B according to the measured blood pressure or the blood pressure estimation index.

As illustrated in FIG. 22, the median nerve E is one of the peripheral nerves of the arm extending from the upper arm to the hand through the carpal tunnel. Stimulating the C-fiber in the median nerve E can activate the parasympathetic nerve to relieve stress. From this, as illustrated in FIG. 8, when the blood pressure adjustment device is mounted on a wrist such that the electrical stimulation unit 130b is located on the median nerve E, it is possible to adjust the blood pressure by stimulating the median nerve E passing through the wrist according to the measured blood pressure or the blood pressure estimation index.

Accordingly, by measuring the blood pressure of the subject or calculating a blood pressure estimation index, which is at least one of a stress index, an autonomic nervous system index, systolic blood pressure, and diastolic blood pressure, from a biological signal of the subject, it is possible to relieve stress and lower the blood pressure of a hypertensive patient. In particular, since it is possible to expect an increase in blood pressure, it is possible to prevent the increase in blood pressure in advance.

Hereinafter, three blood pressure adjustment methods using the blood pressure control device of the present disclosure will be described step by step.

A first blood pressure control method includes the following steps.

First, in a biosignal measurement step, a biosignal including the blood pressure of a subject is measured using the biosignal measurement unit in the state in which the blood pressure control device is disposed on an acupoint area to be stimulated of the subject, that is, an expected acupoint area.

In a stimulus signal generation step, a stimulus signal is generated according to the blood pressure of the subject.

In a stimulus signal application step, the generated stimulus signal is applied to electrodes that stimulate an acupoint area.

After a predetermined time from the application of the stimulus signal, the blood pressure of the subject is measured again so as to determine whether the blood pressure is within a predetermined range from the set reference value. When the blood pressure reaches the range, the application of the stimulus signal may be stopped, and when the blood pressure is out of the range, the application of the stimulus signal may be continued.

A second blood pressure adjustment method includes the following steps.

In a biosignal measurement step, a biosignal of a subject is measured using the biosignal measurement unit in the state in which the blood pressure control device is disposed on an acupoint area to be stimulated of the subject, that is, an expected acupoint area.

In a blood pressure estimation index calculation step, a blood pressure estimation index of a subject is calculated from a biological signal.

In a stimulus signal generation step, a stimulus signal is generated according to the blood pressure estimation index of the subject.

In a stimulus signal application step, the generated stimulus signal is applied to electrodes that stimulate an acupoint area.

After a predetermined time from the application of the stimulus signal, a biosignal of the subject is measured again so as to calculate a blood pressure estimation index, and it is determined whether the blood pressure estimation index is within a predetermined range from the set reference value. When the blood pressure estimation index reaches the range, the application of the stimulus signal may be stopped, and when the blood pressure estimation index is out of the range, the application of the stimulus signal may be continued.

A third blood pressure adjustment method includes the following steps.

In a biosignal measurement step, a biosignal of a subject is measured using the biosignal measurement unit in the state in which the blood pressure control device is disposed on an acupoint area to be stimulated of the subject, that is, an expected acupoint area.

In a blood pressure fluctuation estimation index calculation step, a blood pressure fluctuation estimation index of a subject is calculated from a biological signal.

In a stimulus signal generation step, a stimulus signal is generated according to the blood pressure fluctuation estimation index of the subject.

In a stimulus signal application step, the generated stimulus signal is applied to electrodes that stimulate an acupoint area.

After a predetermined time from the application of the stimulus signal, a biosignal of the subject is measured again so as to calculate a blood pressure fluctuation estimation index, and it is determined whether the blood pressure fluctuation estimation index is within a predetermined range from the set reference value. When the blood pressure fluctuation estimation index reaches the range, the application of the stimulus signal may be stopped, and when the blood pressure fluctuation estimation index is out of the range, the application of the stimulus signal may be continued.

In the foregoing description, specific embodiments of the present disclosure have been described with reference to the accompanying drawings, but it will be apparent that the scope of the present disclosure covers modifications or equivalents based on the technical idea described in the claims.

What is claimed is:

1. An acupoint stimulation device for electrically stimulating an acupoint area of a subject including an acupoint and a portion around the acupoint, the acupoint stimulation device comprising:
    a power supply unit configured to supply power;
    a controller configured to generate an electrical stimulus signal applied to a skin of the subject; and
    an electrical stimulation unit comprising two or more electrodes configured to receive power from the power supply unit and to supply the stimulus signal to the acupoint area, wherein the electrodes are arranged in a state of being electrically insulated from each other and are adapted to be in contact with the skin of the subject,
    wherein the electrical stimulation unit comprises three or more electrodes, and
    the controller is configured to apply the stimulus signal to electrode pairs each comprising two electrodes selected from among the electrodes,
    wherein the controller is configured to alternately apply the stimulus signal to each of the electrode pairs,
    further comprising:
    a temperature sensor unit configured to measure a skin temperature of the acupoint area; and
    a heating unit configured to receive power from the power supply unit so as to increase a temperature of a deep portion of the acupoint area,
    a biosignal measurement unit configured to measure a biosignal of the subject,
    wherein the controller is configured to perform control such that supply of the stimulus signal is stopped when the temperature measured by the temperature sensor unit reaches a set temperature, or wherein the controller is configured to perform control such that power supplied to the heating unit is cut off when the temperature measured by the temperature sensor unit reaches a set temperature,
    wherein the controller is configured to calculate a biometric level from the biosignal measured by the biosignal measurement unit, and to generate the stimulus signal by comparing the calculated biometric level with a preset target biometric level,
    wherein the controller is configured to measure a biopotential of each of the electrodes, calculate a biopotential similarity of each of the electrodes based on the biopotential, then set an electrode pair having a relatively high biopotential similarity as a reference electrode pair, and apply the stimulus signal to the reference electrode pair, and
    wherein the biopotential similarity is calculated as being higher at a position closer to an acupoint than at a position farther from the acupoint.

2. The acupoint stimulation device of claim 1, wherein the electrical simulation unit comprises:
    a wiring layer on which wiring is formed to electrically connect the electrodes to each other; and
    an adhesive layer disposed under the wiring layer and comprising an adhesive adapted to be detachably attached to the skin in the acupoint area, and
    wherein the electrodes are exposed to a bottom surface of the adhesive layer.

3. The acupoint stimulation device of claim 1, wherein the electrical simulation unit comprises:
    a body unit adapted to be detachably attached to the subject and comprising two or more contact terminals configured to be in electrical contact with the acupoint area; and
    a mounting unit coupled to the body unit and comprising the electrodes,
    wherein the electrodes are electrically connected to the contact terminals in a state in which the body unit and the mounting unit are coupled to each other.

4. The acupoint stimulation device of claim 3, wherein the mounting unit is fitted to the body unit.

5. The acupoint stimulation device of claim 3, wherein the mounting unit is aligned in position and coupled to the body unit by magnetic force.

6. The acupoint stimulation device of claim 3, wherein the electrical simulation unit further comprises a fixing unit configured to fix the contact terminals to be in close contact with the skin of the acupoint area.

7. The acupoint stimulation device of claim 6, wherein the fixing unit is formed in a form of a belt or in a form of a band made of an elastic material.

8. The acupoint stimulation device of claim 1, wherein, in the electrical stimulation unit, a distance between centers of two electrodes selected from among the electrodes is 5 mm to 30 mm in order to supply the stimulus signal to the acupoint area.

9. The acupoint stimulation device of claim 1, wherein the biosignal measurement unit comprises a first biosignal measurement unit provided inside the acupoint stimulation device and configured to measure a biosignal from the skin at a location where the electrical stimulation unit is disposed, and
    wherein the controller is a first controller provided inside the acupoint stimulation device.

10. The acupoint stimulation device of claim 1, wherein the biosignal measurement unit comprises a first biosignal measurement unit provided inside the acupoint stimulation device,
    wherein the acupoint stimulation device further comprises:

a stimulation device communication unit provided inside the acupoint stimulation device and configured to transmit the biosignal measured by the first biosignal measurement unit and to receive the stimulus signal; and a user terminal comprising a terminal communication unit configured to receive the biosignal from the stimulation device communication unit and to transmit the stimulus signal, and a second controller configured to generate the stimulus signal according to the biosignal received from the terminal communication unit.

11. The acupoint stimulation device of claim 1, further comprising:

a biometric information collector provided to be spaced apart from the electrical stimulation unit and comprising a second biosignal measurement unit constituting the biosignal measurement unit, and a collector communication unit configured to transmit a biosignal measured by the second biosignal measurement unit;

a user terminal comprising a terminal communication unit configured to receive the biosignal from the collector communication unit and transmit the stimulus signal to the stimulation device communication unit, and a second controller configured to generate the stimulus signal according to the biosignal received from the terminal communication unit; and a stimulation device communication unit provided inside the acupoint stimulation device and configured to receive the stimulus signal.

12. The acupoint stimulation device of claim 1, wherein the heating unit is an induction coil that is disposed in parallel with a skin surface of the acupoint area in a state of being spaced apart from the electrodes so as to form an eddy current in the deep portion.

13. The acupoint stimulation device of claim 1, wherein the heating unit is an LED disposed between the electrodes so as to emit optical energy to the deep portion.

* * * * *